United States Patent [19]

DeSimone et al.

[11] Patent Number: 4,833,088
[45] Date of Patent: May 23, 1989

[54] REAGENT STRIP HANDLING MECHANISM

[75] Inventors: Joseph P. DeSimone, Mishawaka; Robert J. Heiland, Goshen; Joseph L. Moulton, Mishawaka, all of Ind.; D. Glenn Purcell, Edwardsburg, Mich.; Jerry T. Pugh, Elkhart, Ind.

[73] Assignee: Miles Inc., Elkhart, Ind.

[21] Appl. No.: 100,785

[22] Filed: Sep. 25, 1987

[51] Int. Cl.$^4$ .............................................. C12M 1/36
[52] U.S. Cl. ..................... 435/289; 435/291
[58] Field of Search ................ 435/289, 291

[56] References Cited

U.S. PATENT DOCUMENTS

| 3,526,480 | 9/1970 | Findl et al. | 435/291 X |
|---|---|---|---|
| 3,999,948 | 12/1976 | Deindoerfer et al. | 435/291 X |
| 4,250,257 | 2/1981 | Lee et al. | 435/291 X |
| 4,515,889 | 5/1985 | Klose et al. | 435/291 X |

Primary Examiner—Larry Jones
Attorney, Agent, or Firm—Roger N. Coe

[57] ABSTRACT

A quantitative measuring instrument includes a casing with a cavity for a reagent strip handling mechanism. The mechanism includes a slide with a resiliently biased toggle member for providing snap action of the slide between an open, reagent strip loading position and a closed, quantitative measuring position. A light seal is mounted on the toggle member that engages each reagent strip in the closed position of the slide. In a first, alternative embodiment of the instrument, the slide mechanism includes a cam arm that engages cam surfaces on the instrument raising the cam arm to an open, reagent strip loading position from a closed, reagent strip holding position. In this embodiment the slide can be removed from the instrument and cleaned. In a second alternative embodiment the slide includes a first detent corresponding to a closed position of the slide and a second detent corresponding to an open position. A pair of spring fingers are mounted in the cavity of the instrument casing. One of the spring fingers engages the first detent in the closed position and the second spring finger engages the second detent in the open position providing resistance that defines the two positions. The slide in this embodiment can also be removed and cleaned.

15 Claims, 3 Drawing Sheets

U.S. Patent  May 23, 1989  Sheet 1 of 3  4,833,088
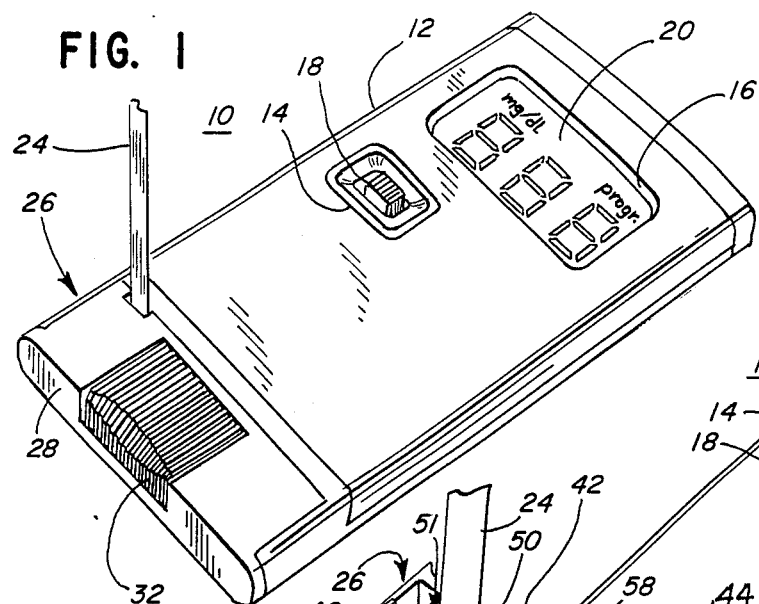
FIG. 1
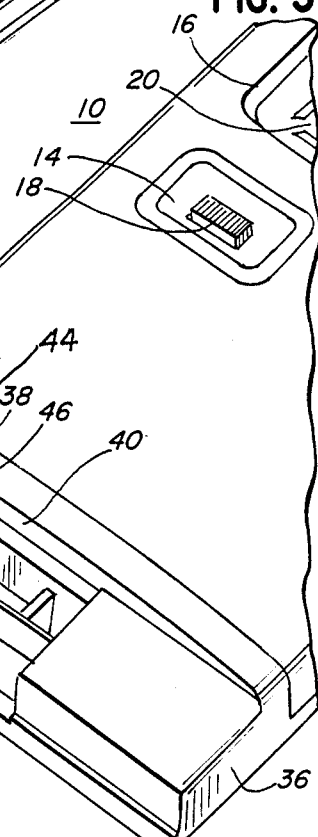
FIG. 3
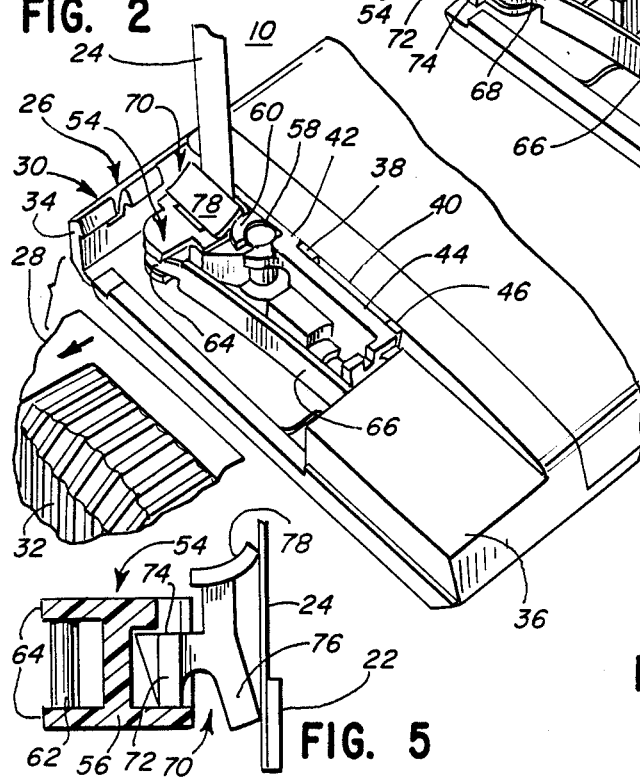
FIG. 2
FIG. 5
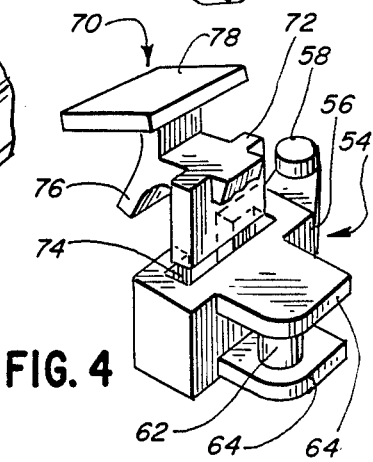
FIG. 4

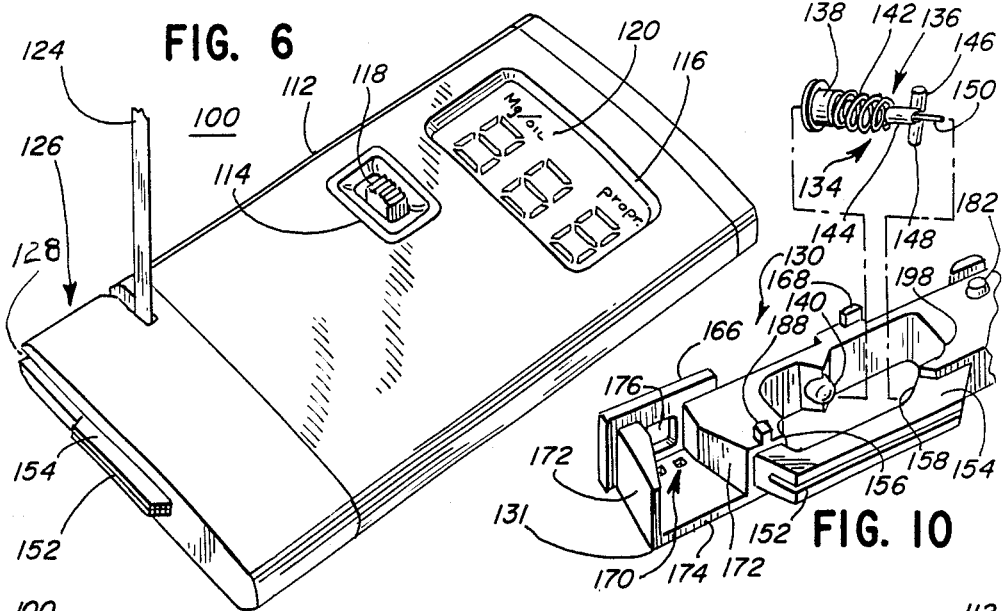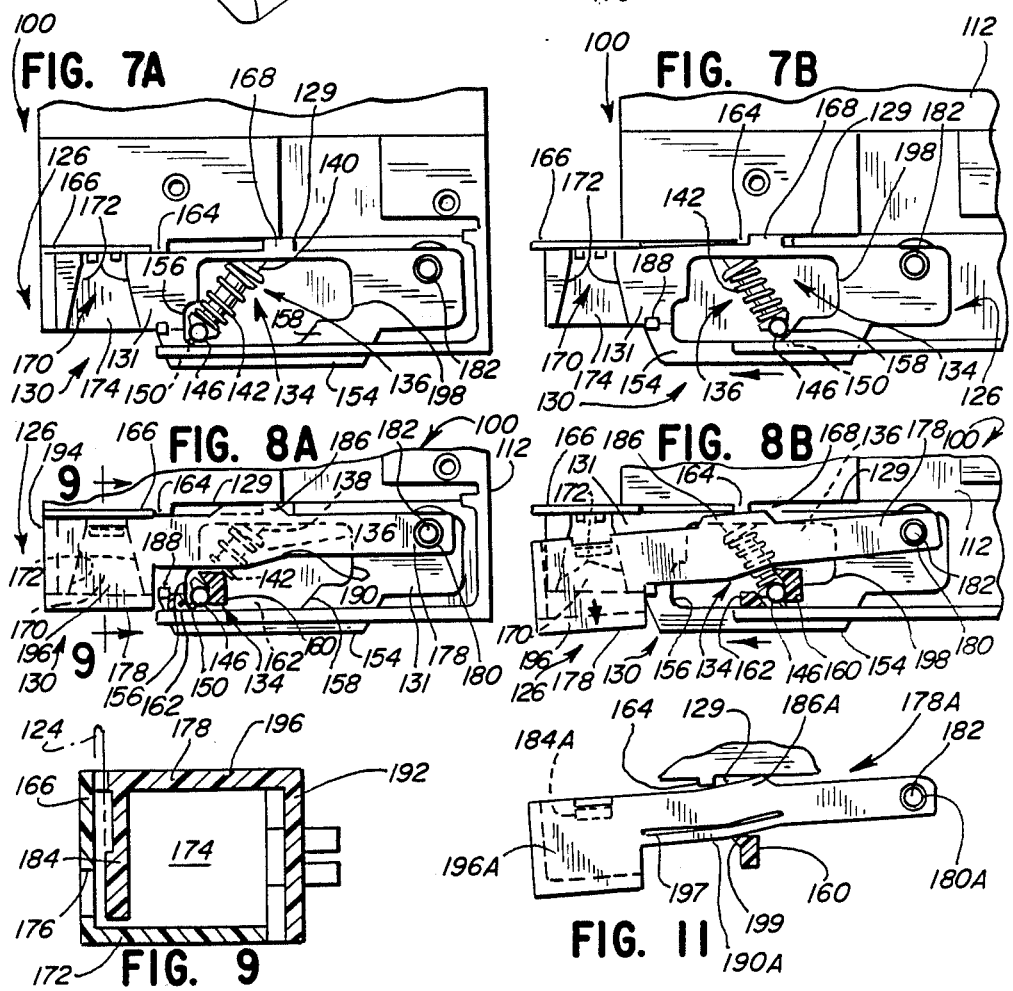

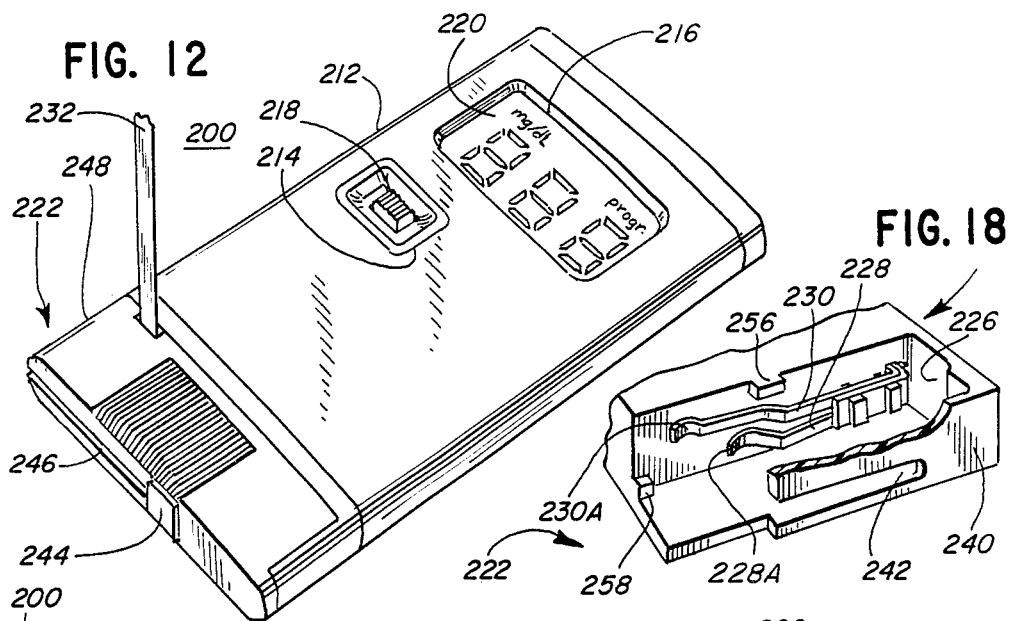
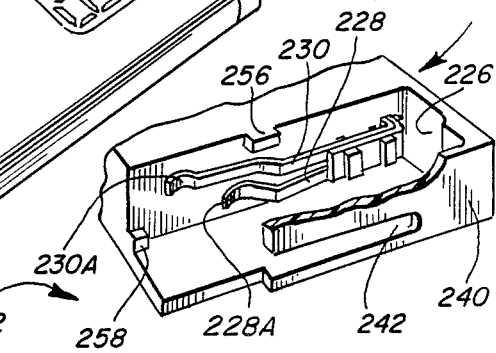
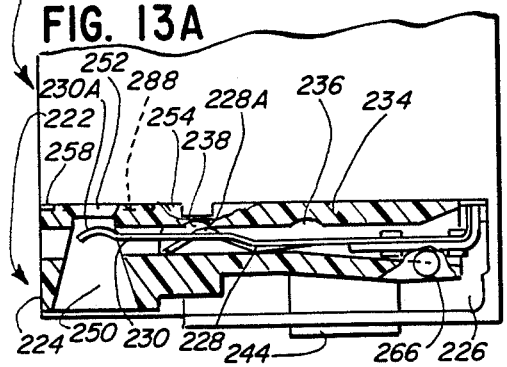
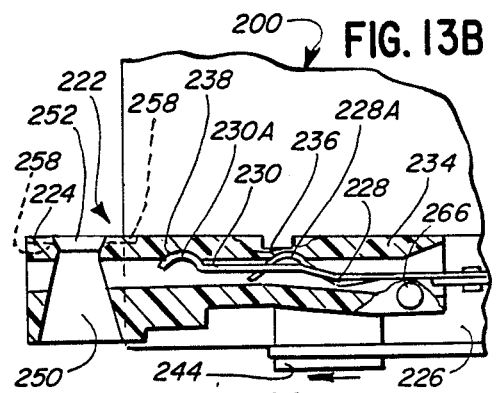
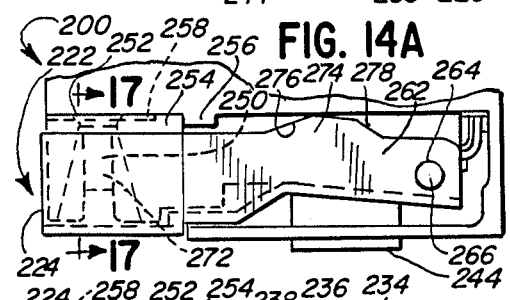
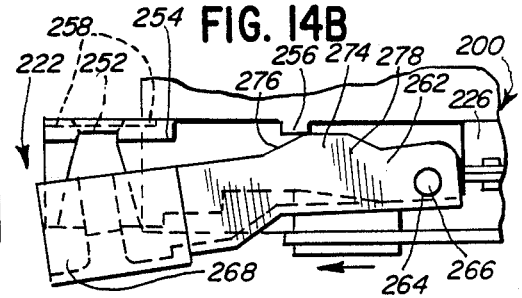
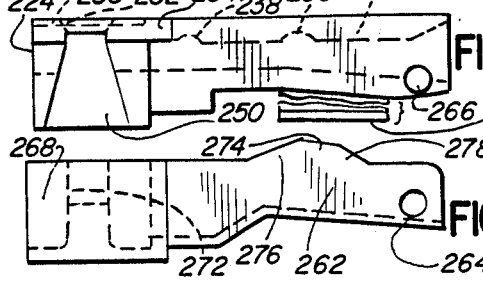
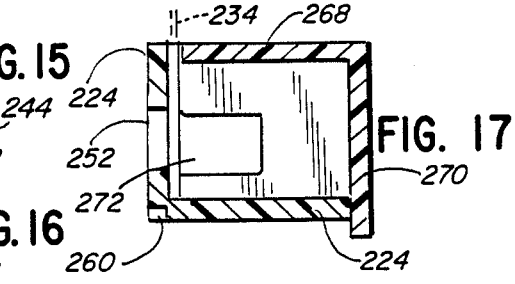

REAGENT STRIP HANDLING MECHANISM

BACKGROUND OF THE INVENTION

1. Field of the Invention

The present invention relates to a new and improved device for handling reagent strips and the like in quantitative measurement instruments; and, more particularly, to a new and improved slide mechanism for portable reflectance photometers moved by positive snap action to one of two positions thereby providing simplified operation.

2. Description of the Background Art

Devices that measure fluctuations in a person's blood sugar, or glucose levels have become everyday necessities for many of the nation's seven million diabetics. Because this disorder can cause dangerous anomalies in blood chemistry and is believed to be a contributor to vision loss and kidney failure, most diabetics need to test themselves periodically and adjust their glucose count accordingly, usually with insulin injections. Patients who are insulin dependent—about 10% to 15% of diabetics—are instructed by doctors to check their blood-sugar levels as often as four times daily.

For years the solution for diabetics was one of several urinanalysis kits that, despite repeated improvements, provided imprecise measurements of glucose in the blood. Examples of early urine testing for glucose are described in U.S. Pat. Nos. 2,387,244 and 3,164,534. Later, reagent strips for urine testing were developed. Testing of urine for glucose, however, is limited in accuracy particularly since the renal threshhold for glucose spillage into the urine is different for each individual. Moreover, sugar (glucose) in urine is a sign that the glucose was too high several hours prior to the test because of the time delay in glucose reaching the urine. Readings taken from the urine, therefore, are indicative of the glucose level in the blood several hours before the urine is tested.

More accurate readings are possible by taking readings directly from blood to determine current glucose levels. Proper dosages of insulin are more obtainable by increasing the frequency of taking the reading. For these reasons, the advent of home blood tests is considered by some to be the most significant advance in the care of diabetics since the discovery of insulin in 1921. Home blood glucose testing was made available with the development of reagent strips for whole blood testing. The reagent strip includes a reactant system comprising an enzyme, such as glucose oxidase, capable of catalyzing the oxidation reaction of glucose to gluconic acid and hydrogen peroxide; an indicator or oxidizable dye, such as o-tolidine; and a substance having peroxidative activity capable of catalyzing the oxidation of the indicator. The dye or indicator turns a visually different shade of color and the shade is an indication of the glucose level. For an accurate reading of the glucose level, a reflectance photometer can be used.

Reflectance photometers measure the degree of color developed on a reagent strip by the glucose contained in a drop of whole blood. The photometer includes a light source. Light emitted by the light source strikes a calibration chip in the instrument providing a first signal used to calibrate the photometer. The calibration step is followed by the light source again emitting light that strikes the reagent area on the reagent strip. Light is reflected into the instrument and is converted to a second electrical signal. A microcomputer computes the first signal to calibrate the instrument and converts the second signal into a direct blood glucose value. This information is displayed digitally.

In order for reflectance photometers to be used by diabetics and other non-technical users, it is important that a user can conveniently calibrate the instrument, load a reacted reagent strip, move the reacted reagent strip into position for reading and read the digital display. It is desirable to provide positive action of the mechanism that calibrates the instrument, loads a reagent strip and reads the reagent strip. This positive action minimizes the possibility for user error. It is also useful to allow for cleaning of those components of the instrument that can become contaminated with patient sample.

To increase the ease of carrying the instrument, thereby allowing more frequent use and helping to control insulin requirements, reflectance photometers are being made smaller and less expensive. Portability also requires an inexpensive and simplified procedure for blocking the leakage of ambient light around the reagent area of the reagent strip during measurement. This ambient light can result in an inaccurate reading by the instrument. It is desirable to provide a low cost component for the instrument that will seal out ambient light from the reagent area during measurement by the instrument.

SUMMARY OF THE INVENTION

An object of the present invention is to provide a new and improved reflectance photometer.

Another object of the present invention is to provide a new and improved reagent strip handling mechanism for reflectance photometers.

A further object of the present invention is to provide a new and improved reagent strip handling mechanism for reflectance photometers that can be removed for cleaning.

A still further object of the present invention is to provide a new and improved reagent strip handling mechanism for reflectance photometers that is portable and requires a minimum of parts.

Still another object of the present invention is to provide a new and improved positive snap action reagent strip handling mechanism for a portable reflectance photometer.

Another object of the present invention is to provide a new and improved reagent strip handling mechanism that includes a light seal for sealing out ambient light from the read head of the instrument while measurements are being performed.

Briefly, the present invention relates to portable reflectance photometers and specifically to reagent strip handling mechanisms for portable reflectance photometers. Instruments of this type are employed to measure the degree of color developed in a reagent pad on a reagent strip. The instrument includes a light source, a read head and related electronics housed in a casing. A reagent strip handling mechanism is provided at one end of the casing for loading a reagent strip and moving the strip adjacent the read head for measurement. The reagent strip handling mechanism includes a slide movable to two different positions. In one position of the slide a reagent strip with a pad may be loaded in the slide. Simultaneously with loading the reagent strip, a calibration chip on the slide is positioned adjacent the read head and the electronics of the instrument are calibrated. In a second position of the slide a reagent pad is positioned adjacent the instrument read head for measurement of the color developed in the pad.

The reagent strip handling mechanism of the present invention allows lay persons and patients to use the portable reflectance photometer with ease and little likelihood of error. This is possible since the reagent strip handling mechanism is moved with positive, snap action between the loading and measuring positions and has a minimum number of components. In a preferred embodiment of the present invention, the snap action is provided by a toggle link and spring. The toggle link and spring provide complete movement of the slide to the loading position and to the measuring position ensuring correct calibration of the electronics of the instrument and accurate measurements of the color developed in the reagent pads. To block ambient light from the area of the read head during the measurement operation of the instrument and to bias the reagent pad to the proper position for measurement, an elastomeric light seal is insert molded on the toggle link. The light seal engages and biases each reagent strip during measurement and is pivoted out of the way during loading of a reagent strip.

The reagent strip handling mechanism can be contaminated or fouled by repeated contact with samples on the reagent pads. This fouling can affect the accuracy of measurements by the instrument. In the past, cleaning these instruments was difficult and often damaging to the electronics of the instrument. First and second alternative embodiments of the present invention, however, provide an instrument with a reagent strip handling mechanism that can be removed from the instrument, cleaned and returned to the instrument for continued use without risk of damage to the instrument or its related electronics. These embodiments also include a calibration or reference chip located in a position that avoids fouling that would interfere with calibrating the instrument. In the first alternative embodiment, a spring toggle is mounted in the reagent strip handling mechanism that provides positive snap action movement of the reagent strip handling mechanism. The reagent slide handling mechanism of the first alternative embodiment includes a cam arm which holds a reagent strip in position during measurement of the color developed in the reagent pad. The cam arm also provides a light shield. The reagent strip handling mechanism with the spring toggle of the first alternative embodiment is self-contained and can be removed from the instrument as a complete unit, and cleaned and returned to the instrument.

In a second alternative embodiment of the present invention, the loading and measuring positions of the reagent strip handling mechanism are defined by a pair of spring fingers that snap into engagement with detents formed in the slide mechanism. A cam arm for holding a reagent strip in position during measurement of the color developed in the reagent pad and for shielding ambient light during the measurement is included. The reagent strip handling mechanism in the second alternative embodiment can be removed as a unit, cleaned and returned to the instrument.

BRIEF DESCRIPTION OF THE DRAWINGS

The above and other objects and advantages and novel features of the present invention will become apparent from the following detailed description of the preferred embodiments of the invention illustrated in the accompanying drawings wherein:

FIG. 1 is a perspective view of a portable reflectance photometer constructed in accordance with the principles of the present invention;

FIG. 2 is an enlarged, partially cut away view of a reagent strip handling mechanism for the portable photometer of the present invention with the mechanism in a first, measuring position;

FIG. 3 is a view similar to FIG. 2 with the reagent strip handling mechanism in a second, reagent strip loading position;

FIG. 4 is an enlarged, perspective view of a toggle link and light seal included in the photometer illustrated in FIGS. 1–3;

FIG. 5 is a partially cut-away, side view of the toggle link and light seal illustrated in FIG. 4 in the first position of the reagent strip handling mechanism;

FIG. 6 is a perspective view of a first alternative embodiment of the portable reflectance photometer illustrated in FIGS. 1–5;

FIG. 7A is a plan view of a slide and a slide handling mechanism for the photometer of FIG. 6 with the slide in a first, reagent pad measuring position;

FIG. 7B is a view similar to FIG. 7A with the slide in a second, reagent strip loading position;

FIG. 8A is a view similar to FIG. 7A showing the slide and a cam arm in the first position of the reagent strip handling mechanism;

FIG. 8B is a view similar to FIG. 8A with the reagent strip handling mechanism in the second, loading position;

FIG. 9 is a view taken along line 9—9 in FIG. 8A;

FIG. 10 is an enlarged, exploded, perspective view of the slide for the photometer illustrated in FIG. 6;

FIG. 11 is a side view of an alternative cam arm that may be used on the slide illustrated in FIG. 10;

FIG. 12 is a perspective view of a second alternative embodiment of the portable reflectance photometer illustrated in FIG. 1;

FIG. 13A is a vertical cross-sectional, plan view of the slide of the photometer illustrated in FIG. 12 in a first, reagent strip measuring position;

FIG. 13B is a view similar to FIG. 13A with the slide in a second, reagent strip loading position;

FIG. 14A is a side view of the slide and cam arm of the second alternative embodiment in a first, reagent strip measuring position;

FIG. 14B is a view similar to FIG. 14A with the slide and cam arm in a second, reagent strip loading position;

FIG. 15 is a side view of the slide used in the reflectance photometer illustrated in FIG. 12;

FIG. 16 is a side view of a cam arm used in the reflectance photometer illustrated in FIG. 12;

FIG. 17 is a view taken along line 17—17 in FIG. 14A; and

FIG. 18 is an enlarged, partially cutaway view of a cavity in the casing of the reflectance photometer illustrated in FIG. 12 into which the reagent strip handling mechanism illustrated if FIGS. 13A–17 is mounted.

DETAILED DESCRIPTION OF PREFERRED EMBODIMENTS

Quantitative measuring instruments such as reflectance photometers are used to measure the degree of color developed on a reagent strip by the glucose contained in a drop of whole blood. The typical photometer includes a light source. Light emitted by the light source strikes a calibration chip in the instrument providing a first signal used to calibrate the photometer. The calibration step is followed by the light source again emitting light that strikes a reagent area on a reagent strip. Light is reflected off the reagent area into the instrument and is converted to a second electrical signal. A microcomputer computes the first signal to calibrate the instrument and converts the second signal into a direct blood glucose value. This information is displayed digitally.

In order for reflectance photometers to be used by diabetics and other non-technical users, it is important that a user can easily calibrate the instrument, load a reacted reagent strip, move the reacted reagent strip into position for reading and read the digital display. It is desirable to provide positive action of the mechanism that calibrates the instrument, loads a reagent strip and reads the reagent strip. This positive action minimizes the possibility for user error. A reflectance photometer with a positive, snap action reagent strip handling mechanism is illustrated in FIGS. 1-5 and generally designated by the reference numeral 10. Reflectance photometer 10 includes a casing 12 with a switch aperture 14 and a display aperture 16. Electronics and a read head are contained within casing 12 for calibrating reflectance photometer 10, reading the color developed in a reagent area on a reagent strip, and computing a blood glucose value. A switch 18 is provided in switch aperture 14 to turn reflectance photometer 10 on and off and to place the reflectance photometer 10 into the desired mode. In LED or similar display 20 is provided in display aperture 16 for displaying the measure blood glucose level.

To load, hold and measure a reagent strip and pad, reflectance photometer 10 includes a reagent strip handling mechanism 26. Included with the handling mechanism 26 is a cover 28 that fits over and is secured to a slide assembly 30 (FIG. 2). Slide assembly 30 slides or moves between a first, closed position (FIGS. 1 and 2) and a second, open position (FIG. 3). In accordance with the present invention, slide assembly 30 moves with positive, snap action between the first and second positions thereby minimizing the possibility of moving the slide assembly 30 to a position intermediate the first and second positions resulting in inaccurate measurements. Cover 28 is provided with a grooved or roughened surface 32 allowing the placement of a thumb to apply a force to move cover 28 and slide assembly 30 between the first and second positions.

Referring to FIG. 2, slide assembly 30 includes a slide housing 34 that slides within an upper portion 36 of casing 12. To prevent over insertion or over extension of the slide housing 34, it is desirable to provide a positive stop or limit at each of the first and second positions. These limits are defined by a first stop 38 integrally formed on a slide surface 40 in upper portion 36. First stop 38 cooperates with a second stop 42 formed on the bottom 44 of slide housing 34 and with a third stop 46 also formed on bottom 44. In the first, closed position of slide assembly 30, first stop 38 engages second stop 42 (FIG. 2) thereby positively defining the first position of slide assembly 30 and preventing over insertion of slide housing 34 into upper portion 36. In the second, open position of slide assembly 30, first stop 38 engages third stop 46 (FIG. 3) and positively defines the first position. The engagement of first stop 38 and third stop 46 prevents over extension of slide housing 34 out of upper portion 36.

As best illustrated in FIG. 3, the second, open position of slide assembly 30 is the position for loading a reagent strip 24 into the slide assembly 30 and for calibrating the electronics of instrument 10. To calibrate instrument 10 a calibration or reference chip (not shown) is secured to the underside of bottom 44 at a location behind the second stop 42. In the second position of slide assembly 30 the calibration chip is aligned with a read head (not shown) in the instrument 10. By locating the reference or calibration chip on the underside of slide assembly 30 user access to the chip is limited. In addition, the exposure of the chip to contaminants, such as blood, is limited and misuse or damage to the chip is prevented ensuring proper and accurate calibration of the instrument 10.

To hold a reagent strip, slide assembly 30 includes a pair of flanges 48 and 50 which define a reagent strip holding section 51 for holding a reagent pad 22 (FIG. 5) and reagent strip 24. Flanges 48 and 50 are spaced from each other to define an opening 52. An aperture is formed in the bottom 44 of slide housing 34 between flanges 48 and 50. Once a reagent strip 24 is placed in the reagent holding section 521, the reagent pad 22 is positioned on and over the aperture. When slide assembly 30 is moved to the first position (FIGS. 1 and 2), the aperture in bottom 44 and reagent pad 22 are positioned over and adjacent to the read head allowing a measurement of the color developed in reagent pad 22. The aperture in bottom 44 also allows a user to check the position of reagent pad 22 in the second position of slide assembly 30 to be sure the reagent pad 22 is properly positioned in the reagent strip holding section 51. Since read heads are height sensitive, the calibration ship and reagent pad 22 are positioned on the slide housing 34 to be the same distance above the read head in the second and first positions, respectively, thereby ensuring proper readings and eliminating reading error.

It is intended that a patient or lay person can use instrument 10 with little or no difficulty. Since instrument 10 is intended for use by inexperienced users as well as experienced users, it is preferable that slide assembly 30 have positive, snap action movement between the first and second positions preventing partial movement between these positions. Positive, snap action is provided in instrument 10 by a toggle assembly generally designated by the reference numeral 54. As is best seen in FIG. 5, toggle assembly 54 includes a toggle link 56 fabricated of any rigid plastic that is not wearable since it will be sliding and engaging metal and plastic surfaces and parts. Toggle link 56 is secured to slide housing 34 by a first dowel or pivot pin 58 that is rotatably held by a snap fit in a clevis 60 formed on slide housing 34.

Toggle link 56 also includes a second dowel or pivot pin 62 positioned between a pair of side portions 64 of toggle link 56. Pivot pin 62 is mechanically connected to casing 12 by a spring 66 secured at a first end to upper portion 36 of casing 12. A second end 68 of spring 66 is cup-shaped and engages and partially encircles second pivot pin 62. Spring 66 imparts a bias to second pivot pin 62 generally toward the bottom 44 of slide housing 34.

Due to the connection of pivot pin 58 with slide housing 34 and pivot pin 62 with spring 66, slide housing 34 and first pivot pin 58 move relative to second pivot pin 62 and second end 68 of spring 66 as slide housing 34 is moved from the first position (FIGS. 1 and 2) to the second position (FIG. 3) and from the second position to the first position. During movement of slide housing 34, spring 66 acts in conjunction with toggle link 56 to provide positive, snap action of slide assembly 30. As slide assembly 30 is moved, toggle link 56 pivots at pivot pin 58. In the first, closed position of slide assembly 30, spring 66 biases toggle link 56 into engagement with a reagent strip 24 holding the reagent strip 24 in position for a reading by the read head. As slide assembly 30 is moved by a user from the first position to the second position, spring 66 is flexed in a direction generally away from bottom 44. Once toggle link 56 moves over-center, spring 66 acts to move the toggle link 56 to the up or open position snapping the slide assembly 30 to the second, open position (FIG. 3). The reverse of this procedure occurs as slide assembly 30 moves from the second position to the first position. The snap action of the toggle-spring combination provides positive action of slide assembly 30 to both the first and second positions to ensure correct calibration and measurement by instrument 10. This snap action provides a simplified operation technique of instrument 10 allowing an untrained patient or lay person to use and operate instrument 10 with little likelihood of erroneous readings.

Accurate readings by the read head require that the reagent pad 22 be biased against the aperture in bottom 44 of slide housing 34. Accurate readings also require minimizing ambient light leaking into the instrument 10 while measurements are being performed in the first position First stop 38, second stop 42 and third stop 46 provide an ambient light seal but additional light sealing is preferred. The proper amount of biasing of reagent pads along with a light and dust seal are provided by a single light shield or seal 70. Light seal 70 is fabricated of a resilient elastomer allowing it to flex to provide a bias on the reagent strip 24 and pad 22 during measurement in the first position. In a preferred embodiment, light seal 70 is a silicone rubber that is resistant to blood and chemicals.

Light seal 70 includes a base 72 that is mounted by insert molding in a T-shaped slot 74 formed in toggle link 56 (FIGS. 4 and 5). Light seal 70 further includes a first arm 76 (FIG. 5) that extends through opening 52 between flanges 48 and 50 in the first position of instrument 10 to engage a reagent strip 24 behind the reagent pad 22. First arm 76 biases reagent pad 22 against the aperture in bottom 44. A second arm or shield 78 (FIGS. 2 and 3). is also provided on light seal 70. Shield 78 engages reagent strip 24 above reagent pad 22 (FIG. 5). Second arm 78 is wider than reagent strip 24 and in the second position of slide assembly 30, engages reagent strip 24 and the bottom 44 of slide housing 34 on both sides of reagent strip 24 providing a seal that seals out ambient light and dust from reagent pad 22 and the read head. When instrument 10 is not being used, light seal 70 seals the area around the read head from dust.

Turning now to FIGS. 6-11 a first alternative reflectance photometer 100 is illustrated. Instrument 100 is similar to instrument 10 in that it includes a casing 112 with a switch aperture 114 and a display aperture 116. A switch 118 is provided for turning the instrument 100 on and off and to place the instrument 100 in the desired mode of operation. An LED or similar display 120 is mounted in the display aperture 116. Instrument 100 includes the same electronics and read head as instrument 10.

As with instrument 10, instrument 100 is used to measure the degree of color developed on a reagent pad on a reagent pad on a reagent strip 124. Instrument 100 includes a reagent strip handling mechanism 126 into which a reagent strip 124 is loaded (FIGS. 7B and 8B) and held during measurement of the degree of color on the reagent pad (FIGS. 7A and 8A). Slide assembly 130 is mounted in the upper portion of casing 112 and includes a slide 131 that can be moved from a first, reagent pad measuring position (FIGS. 6, 7A and 8A) to a second, reagent strip loading position (FIGS. 7B and 8B) by sliding on a sliding surface 129 defined on casing 112.

Slide assembly 130 moves with positive, snap action between the first and second positions minimizing user error. Positive, snap action is provided by a spring toggle generally designated by the reference numeral 134. As best seen in FIG. 10, spring toggle 134 includes a three-piece post 136 defined by a tubular spring holder 138 mounted on a numb 140 formed on slide 131, a spring 142 mounted on and encircling tubular spring holder 138, and a T-shaped post member 144 with arms 146 and 148. Post 136 is mounted in slide 131 by mounting spring 142 around spring holder 138, inserting the T-shaped post member 144 into spring holder 138 and placing spring holder 138 over and onto nub 140. The T-shaped post member 144 includes a guide pin 150 that is positioned in a track 152 formed in a thumb actuator 154 on slide 131. The guide pin 150 is biased into track 152 and the spring holder 138 is biased onto numb 140 by spring 142. This biasing action holds spring toggle 134 in slide 131.

In the embodiment illustrated in FIGS. 6-8B, thumb actuator 154 extends through a slot 128. Spring toggle 134 provides positive, snap action of slide assembly 130 between the first and second positions. This positive, snap action simplifies use of instrument 100 and minimizes user error. The snap action snaps slide assembly 130 between a first abutting surface 156 formed on slide 131 and a second abutting surface 158 formed on thumb actuator 154. When arm 146 and arm 148 of post member 144 are engaging first abutting surface 156, slide aseembly 130 is in the first position (FIGS. 7A and 8A). Slide assembly 130 is in the second position when arms 146 and 148 are engaging second abutting surface 158 (FIGS. 7B and 8B).

Spring toggle 134 is moved between the first position (FIGS. 7A and 8A) and the second position (FIGS. 7B and 8B) by movement of slide assembly 130 and engagement with a first stop 160 integrally molded on the inner surface of casing 112 and a pin or second stop 162 also on casing 112. As best illustrated in FIGS. 8A and 8B, as the slide assembly 130 is moved from the first position to the second position, spring holder 138 moves with slide 131 and pivots on nub 140 while post member 144 remains stationary since it is held by first stop 160 and second stop 162. As slide assembly 130 moves, pin 150 moves along track 152. The engagement of arms 146 and 148 moves post member 144 into spring holder 138 compressing spring 142. As arms 146 and 148 move past the equidistant or center point between first abutting surface 156 and second abutting surface 158, spring toggle 134 moves over-center. As spring toggle 134 moves over-center, spring 142 applies a positive, snap action force on the three-piece post 136 moving slide assembly 130 from the first position to the second position and preventing slide assembly 130 from stopping at a position intermediate the first and second positions. A similar sequence occurs, but in reverse, upon moving slide assembly 130 from the second position to the first position.

To define the first and second positions of slide assembly 130 and to discourage or prevent over insertion or over extension of slide assembly 130 during use, a first limit stop 164 is defined on sliding surface 112. As slide assembly 130 reaches the first position, first limit stop 164 engages an aperture plate 166 formed on slide 131. As best illustrated in FIG. 10, aperture plate 166 is secured to or integral with the underside of slide 131. As slide assembly 130 reaches the second position, first limit stop 164 engages a second limit stop 168 (FIG. 7B) formed on slide 131. Engagement of first limit stop 164 and second limit stop 168 positively defines the second position of slide assembly 130 halting further movement of slide assembly 130 and avoiding over extension.

Use of instrument 100 is further simplified by the easy loading of a reagent strip in slide assembly 130, calibration of the instrument and measurement of the color developed in the reagent pad. In the second position of slide assembly 130 (FIGS. 7B and 8B), a reagent strip 124 can be loaded while a reference chip (not shown) located on the underside of slide 131 between aperture plate 166 and second limit stop 168 is aligned with the instrument read head for calibration of the electronics of instrument 100. A reagent strip 124 is loaded in slide assembly 130 by insertion into a reagent pad holding section 170 defined on slide 131 between a pair of side walls 172 and a back wall 174 (See FIG. 10). The pad of the loaded reagent strip 124 is positioned in alignment with and against an aperture 176 in aperture plate 166. The reagent pad holding section 170 ensures proper alignment of the raagent pad with the read head in the first position of slide assembly 130 while avoiding direct contact of the pad with the read head.

Consistently accurate readings by the read head requires that the reagent pads of the reagent strips 124 be biased against aperture plate 166 and over aperture 176 during measurements taken by the read head. In slide assembly 130 each reagent pad is biased against aperture plate 166 by a cam arm 178 (FIGS. 7A and 7B). Cam arm 178 is pivotally mounted on slide 131 by an aperture 180 that is positioned on a button 182 integrally molded on slide 131. Cam arm 178 includes a finger 184 (FIG. 9) which in the first position of slide assembly 130, engages the reagent strip 124 behind the reagent pad biasing the reagent pad against aperture plate 166 and aperture 176.

In the second position of slide assembly 130, cam arm 178 and finger 184 are moved to a position away from aperture plate 166 allowing a reagent strip 124 to be loaded into position (FIG. 8B). Cam arm 178 is moved to this loading position by the interaction of a first cam surface 186 on cam arm 178 with the first limit stop 164. As slide assembly 130 is moved from the first position (FIG. 8A) to the second position (FIG. 8B), first limit stop 164 engages cam surface 186 and pivots cam arm 178 about button 182 raising finger 184 from the aperture plate 166. The extent of the pivoting of cam arm 178 and the rising of finger 184 is limited by engagement of cam arm 178 with a cam arm stop 188 molded on slide 131. The sizes, configurations and locations of cam arm stop 188, first limit stop 164 and first cam surface 186 are predetermined to hold cam arm 178 in the raised position and prevent wobbling during loading of a reagent strip 124.

Once a reagent strip 124 has been loaded in the reagent holding section 170, slide assembly 130 is moved to the first position. As this occurs, cam arm 178 and finger 184 are pivoted into engagement with the reagent strip 124. Cam arm 178 is pivoted into engagement with the reagent strip through the interaction of a second cam surface 190 on cam arm 178 and the first stop 160. In the first position of slide assembly 131, engagement of first limit stop 160 and cam arm 178 firmly holds finger 184 against reagent strip 124 (FIG. 8A).

While a measurement is performed by the read head in the first position of reagent strip handling mechanism 130, it is desirable that ambient light be blocked from the read head and reagent pad areas. Cam arm 178 includes a top wall 192, a front wall 194 and a back wall 196 that function with side walls 172 and back wall 174 of reagent pad holding section 170 to form an enclosure around the reagent pad and read head. This enclosure serves to block ambient light during measurement of the color developed in the reagent pad.

An additional feature of instrument 100 is the ability to remove slide assembly 130 for cleaning. After several uses of instrument 100, blood and other contaminants can accumulate on the slide 131, cam arm 178 and the reference chip. This build up can affect the accuracy of measurements taken by instrument 100. Since cleaning the entire instrument 100 can damage the sensitive electronics housed in casing 112, slide assembly 130 is removable allowing cleaning without damaging the electronics housed in casing 112. Slide assembly 130 can be removed by grasping and lifting the portion of the slide 131 and cam arm 178 extending outside of casing 112 while the slide assembly 130 is in the second position. This action lifts second limit stop 168 over first limit stop 164 allowing slide assembly 130 to be withdrawn from casing 112. As slide assembly 130 is withdrawn, pin 162 maintains contact with arm 146 moving pin 150 along track 152 and arm 146 into engagement with a third abutting surface 198 defined on slide 131. Spring 142 biases arms 146 and 148 into engagement with third abutting surface 198 once slide assembly 130 is withdrawn from casing 112 and guide pin 150 remains in track 152 preventing spring toggle 134 from falling out of slide assembly 130. Once slide assembly 130 is removed from casing 112, cam arm 178 can be taken off of slide 131 to facilitate cleaning. Once slide 131 and cam arm 178 have been cleaned, cam arm 178 is mounted on slide 131 and the assembled slide assembly 130 is inserted into casing 112. As slide assembly 130 is repositioned into casing 112, arm 146 moves under pin 162 and engages an inclined surface 199 on first stop 160. Arm 146 moves up the inclined surface 199 into engagement with first stop 160. As slide assembly 130 is inserted further into casing 112, arm 146 is moved out of abutment with third abutting surface 158. In this position, instrument 100 is again ready for use.

Turning now to FIG. 11, an alternative embodiment of cam arm 178 is illustrated. To ensure the proper biasing force against the reagent pad during the measuring operation, close tolerances in fabricating cam arm 178 are required. To reduce the need for these close tolerances and to provide a larger spring biasing force on the reagent pad, alternative cam arm 178A (FIG. 11) can be used. Cam arm 178A is substantially identical to cam arm 178 and parts of cam arm 178A that are the same as the corresponding parts on cam arm 178 are identified by the same reference numeral appearing in FIGS. 6–9 but with a suffix "A".

Cam arm 178A differs from cam arm 178 by the inclusion of a slot 197 extending along the length of cam arm 178A and below second cam surface 190A. In the first position of instrument 100, first stop 160 engages second cam surface 190A flexing cam arm 178A and partially collapsing slot 197. This deflection or collapsing slot 197 produces a mechanical spring action providing a biasing force on a reagent pad through finger 184A. This deflection also allows compensation for any variance in the size of cam arm 178A that would prevent or resist movement of slide assembly 130 to the first position due to engagement with first stop 160 with the second cam surface 190.

Reference is now directed to FIGS. 12-18 and specifically to a second alternative embodiment of the reflectance photometer designated by the reference numeral 200. Instrument 200 includes a casing 212, a switch aperture 214, a display aperture 216, a switch 218 and a display 220. Instrument 200 further includes a modified reagent strip handling mechanism 222. The reagent strip handling mechanism 222 includes a slide 224 that can be removed from the instrument 200 and cleaned similar to that of slide 131. A calibration chip is mounted on slide 224 and this also can be cleaned.

Slide 224 is slideably mounted in a cavity 226 formed in casing 212. As seen in FIG. 18, secured within cavity 226 are a first spring finger 228 and a second spring finger 230 that function to define a first, closed position of slide 224 (FIG. 13A) and a second, loading position of slide 224 (FIG. 13B). First spring finger 228 also functions to bias a reagent pad on a reagent strip 232 into position during the measuring operation of instrument 200 (FIGS. 12, 13A and 14A). Each spring finger 228 and 230 includes an undulation portion 228A and 230A, respectively. As best illustrated in FIGS. 13A and 13B, slide 224 includes a bottom wall 234 with a first detent or depression 236 formed in the bottom wall 234. A second detent or depression 238 is also formed in bottom wall 234 at a position spaced from detent 236. In the first position of slide 224 (FIG. 13A) undulation 228A is located in detent 238. The interaction of undulation 228A and detent 238 provides a positive stop and a resistance to movement of slide 224 which defines the first or loading position of slide 224. In the second position of slide 224 (FIG. 13B) undulation portions 228A and 230A are positioned in first detent 236 and second detent 238, respectively. In this position first spring finger 228 and second spring finger 230 provide a positive stop and resistance to movement of slide 224 and define the second or measuring position of slide 224.

To move slide 224, casing 212 includes a wall 240 with a slot 242 through which a handle 244 on slide 224 extends. Handle 244 also extends through a slot 246 formed in a cover 248 that encloses cavity 226. A user of instrument 200 can move slide 224 between the first and second positions by moving handle 244 along slot 246.

To use instrument 200, a reagent strip 232 is loaded into a reagent strip holding section 250 of slide 224 while slide 224 is in the first position. Once a reagent strip 232 is loaded, slide 224 is moved to the first position (FIG. 13A). As slide 224 is moved, the reagent strip 232 engages and moves under the undulation 230A. As the first position of slide 224 is reached, undulation 228A snaps into detent 238 holding slide 224 in the first position. In the first position, undulation 230A biases the reagent pad of reagent strip 232 against an aperture 252 in bottom wall 234 of slide 224. Aperture 252 is aligned with the read head in instrument 200 allowing measurement of the color developed in the reagent pad.

To prevent over insertion of slide 224 beyond the first position, slide 224 includes a flange 254 that engages a first stop 256 on casing 212 (FIG. 14A). Over extension of slide 224 beyond the second position is prevented by a second stop 258 formed in cavity 226. A track 260 (FIG. 17) is fabricated in slide 224 and as slide 224 is moved between the first and second positions track 260 moves over second stop 258. Upon slide 224 reaching the second position, second stop 258 engages the end of the track 260 preventing further extension of slide 224 out of cavity 226.

As mentioned, instrument 200 includes the capability of removing slide 224 for cleaning. This allows cleaning of the parts of instrument 200 most likely to become fouled while protecting the electronics of instrument 200 from damage that could result from exposure to cleaning fluids. Slide 224 is easily removed from cavity 226 by moving slide 224 to the second position (FIG. 13A) and lifting slide 224 upward over first stop 256 and second stop 258. Once slide 224 has cleared first stop 256 and second stop 258 it can be withdrawn from cavity 226 and cleaned. This procedure is reversed to replace slide 224 in cavity 226.

Reagent strip handling mechanism 222 also includes a cam arm 262 that functions to guide the reagent strip 232 during loading and to hold reagent strip 232 by a finger 171 during measurement of the color developed in the reagent pad. Cam arm 262 includes an aperture 264 that is positioned over a button 266 formed on slide 224 coupling cam arm 262 to slide 224 while allowing cam arm 262 to pivot about button 266.

To load a reagent strip 232 in the second position of the reagent strip handling mechanism 222, cam arm 262 is pivoted away from the bottom wall 234 by the engagement of a cam surface 274 with first stop 256 (FIG. 14B). Cam surface 274 includes a first inclined surface 276 and a second inclined surface 278. As slide 224 is moved from the first position (FIG. 14A) to the second position (FIG. 14B), first inclined surface 276 engages first stop 256 smoothly pivoting cam arm 262 away from bottom wall 234. If slide 224 and cam arm 262 are removed from the instrument 200 for cleaning, upon return of slide 224 and cam arm 262 to cavity 226, second inclined surface 278 will engage first stop 256 pivoting the cam arm 262 and allowing cam surface 274 to pass smoothly over first stop 256.

Cam arm 262 provides the additional function of blocking ambient light from a read head in instrument 200 and a reagent pad during the measurement operation. To provide a shield to block ambient light, cam arm 262 includes a side wall 268 and a top wall 270 that form an enclosure around the reagent pad in the first position of slide 224.

Many modifications and variations of the present invention are possible in light of the above teachings. Thus, it is to be understood that, within the scope of the appended claims, the invention may be practiced other than as specifically described.

What is claimed is:

1. A reagent strip handling mechanism for reflectrance photometers and the like, comprising:
 a housing,
 means for quantitative measurement of a reagent area on a reagent strip,
 a slide mechanism on said housing,
 means for allowing said slide mechanism to be moved between an open, reagent strip receiving position and a closed, reagent area measuring position; and a toggle assembly on said slide assembly providing positive snap action of said slide mechanism between said open and closed positions.

2. A reagent strip handling mechanism as claimed in claim 1 wherein said slide mechanism includes a track for said toggle assembly, a first stop in said track, a second stop in said track, a third stop in said track, a spring biased post pivotally mounted in said track, said post including a first end movable between said first, second and third stops, first cam means for engaging said first end of said post upon movement of said slide mechanism.

3. A reagent strip handling mechanism as claimed in claim 1 further comprising a light seal element on said toggle assembly, said light seal element including a first portion engaging said reagent strip in said closed position of said slide mechanism for sealing ambient light from said reagent area, said light seal element including a second, biasing portion engaging said reagent strip in said closed position of said slide mechanism and biasing said reagent area toward said quantitative measuring means.

4. A reagent strip handling mechanism as claimed in claim 1 further comprising means for allowing said slide mechanism to be removed from said housing.

5. A reagent strip handling mechanism as claimed in claim 1 further comprising a cam arm pivotally mounted on said slide mechanism, said cam arm including a reagent strip holding portion, a first cam surface on said cam arm, a first cam on said housing located to engage said first cam surface upon movement of said slide mechanism to said open position moving said reagent strip holding portion to a reagent strip loading position, a second cam surface on said cam arm, a second cam on said housing located to engage said second cam surface upon movement of said slide mechanism to said closed position moving said reagent strip holding portion into engagement with said reagent strip.

6. A reagent strip handling mechanism as claimed in claim 1 wherein said toggle assembly includes a toggle member with a first toggle arm mounted on said slide, said toggle member including a second arm, a biasing member mounted on said housing, said second arm engaging said biasing member.

7. An innovative slide mechanism integral with a portable spectrophotometer, said mechanism providing a transporting means for moving a reagent test strip into an optics chamber of said spectrophotometer to obtain a spectrophotometric reading of said test strip and to thereafter transport said strip away from said chamber for removal and disposal of said reagent test strip, said mechanism consisting essentially of:
a housing defining a slot, said slot having a forward position and a rearward position;
a reagent test strip receiving member slideably position within said slot between the slot's forward and rearward position, whereby a reagent test strip can be placed into or removed from said receiving member when said member is in said forward position and whereby said reagent test strip is placed in proper alignment within said spectrophotometer optics chamber such that a reflectance measurement can be taken when said test strip and receiving member are slid into said rearward position;
a biasing means for providing said reagent test strip receiving member a snap action movement between said forward and rearward position;
whereby said receiving member has an opening, said opening including a first stop, a second stop and a third stop;
a position means comprising a toggle member mounted in said slide opening for selected engagement with said first stop, said second stop and said third stop, whereby said biasing means biases said toggle post into engagement with one of said first stop, said second stop and said third stop;
a first cam means for engaging said toggle post upon movement of such slide and moving said toggle post into engagement with one of said first stop and said second stop; and
a second cam means for engaging said toggle post and moving said toggle post into engagement with said third stop upon sliding said receiving member into said forward position.

8. An innovative slide mechanism integral with a portable spectrophotometer, said mechanism providing a transporting means for moving a reagent test strip into an optics chamber of said spectrophotometer to obtain a spectrophotometric reading of said test strip and to thereafter transport said strip away from said chamber for removal and disposal of said reagent test strip, said mechanism consisting essentially of:
a housing defining a slot, said slot having a forward position and a rearward position;
a reagent test strip receiving member slideably position within said slot between the slot's forward and rearward position, whereby a reagent test strip can be placed into or removed from said receiving member when said member is in said forward position and whereby said reagent test strip is placed in proper alignment within said spectrophotometer optics chamber such that a reflectance measurement can be taken when said test strip and receiving member are slid into said rearward position;
a biasing means for providing said reagent test strip receiving member a snap action movement between said forward and rearward position;
a cam arm pivotally mounted on said test strip receiving member, said cam arm including a first cam surface and a second cam surface;
a first cam means for engaging said first cam surface and pivoting said cam arm to a first position corresponding to said forward position; and
a second cam means for engaging said second cam surface and pivoting said cam arm to a second position corresponding to said rearward position.

9. The mechanism of claim 8 wherein said cam arm includes a slot.

10. The mechanism of claim 9 further comprising a sealing means for sealing a reagent strip from ambient light in said rearward position.

11. The mechanism of claim 10 wherein the light seal is mechanically coupled with and moveable with said position defining means, said light seal including sealing means for at least partially surrounding a portion of a reagent strip to seal ambient light from said portion.

12. The mechanism of claim 11 wherein said test strip receiving member further comprises a read head aperture, and means for biasing a reagent strip against said read head aperture in said rearward position.

13. The mechanism of claim 12 wherein said biasing means comprises a resilient member operable by said position defining means.

14. The mechanism of claim 13 further comprising a light reference element on said reagent strip receiving member, said mechanism further comprising a first limit and means for engaging said first limit to limit the movement of said slide mechanism.

15. The mechanism of claim 14 wherein said position defining means includes a first spring finger, means for releasably holding at least a portion of said spring finger in said reagent strip receiving position, a second spring finger and means for releasably holding at least a portion of said second spring finger in said reagent strip in said rearward position.

* * * * *